United States Patent
Westrin (10) Patent No.: US 11,083,734 B2
(45) Date of Patent: Aug. 10, 2021

(54) DEXAMETHASONE ORAL FILM

(71) Applicants: ACUCORT AB, Helsingborg (SE); LTS LOHMANN THERAPIE-SYSTEME AG, Andernach (DE)

(72) Inventor: Bengt Arvid Westrin, Lund (SE)

(73) Assignees: ACUCORT AB, Helsingborg (SE); LTS LOHMANN THERAPIE-SYSTEME AG, Andernach (DE)

( * ) Notice: Subject to any disclaimer, the term of this patent is extended or adjusted under 35 U.S.C. 154(b) by 144 days.

(21) Appl. No.: 16/213,617

(22) Filed: Dec. 7, 2018

(65) Prior Publication Data

US 2019/0175617 A1 Jun. 13, 2019

Related U.S. Application Data

(63) Continuation of application No. 15/523,502, filed as application No. PCT/EP2015/075697 on Nov. 4, 2015, now abandoned.

(30) Foreign Application Priority Data

Nov. 4, 2014 (DK) .......................... PA 2014 70674

(51) Int. Cl.

| A61K 31/573 | (2006.01) |
| A61K 9/00 | (2006.01) |
| A61K 47/38 | (2006.01) |
| A61K 9/70 | (2006.01) |

(52) U.S. Cl.
CPC .......... *A61K 31/573* (2013.01); *A61K 9/0056* (2013.01); *A61K 9/7007* (2013.01); *A61K 47/38* (2013.01)

(58) Field of Classification Search
None
See application file for complete search history.

(56) References Cited

U.S. PATENT DOCUMENTS

| 2005/0147653 A1 | 7/2005 | Yasuda et al. | |
| 2008/0220029 A1 | 9/2008 | Ng et al. | |
| 2009/0035375 A1* | 2/2009 | Skrtic | A61K 9/0095 424/484 |
| 2011/0009834 A1* | 1/2011 | Asmussen | A61K 9/2072 604/289 |
| 2011/0244047 A1* | 10/2011 | Asari | A61K 31/4045 424/489 |
| 2011/0262520 A1* | 10/2011 | Dormady | A61K 31/4439 424/443 |
| 2014/0155483 A1 | 6/2014 | Li et al. | |
| 2017/0304319 A1 | 10/2017 | Westrin | |

FOREIGN PATENT DOCUMENTS

| CN | 101626757 A | 1/2010 |
| EP | 1 504 765 A1 | 2/2005 |
| JP | 2007-533697 A | 11/2007 |
| WO | WO-2005/102287 | 11/2005 |
| WO | WO-2013/015545 A1 | 1/2013 |

OTHER PUBLICATIONS

Nishigaki, international Journal of Pharmaceutics, 424, 2012 (Year: 2012).*
Methocel, Dow, 2013 (Year: 2013).*
"USP Hypromellose Pharmacoat," Shin Etsu Chemical Co., Ltd. (2004) pp. 1-11.
Chambin et al., "Effects of different cellulose derivatives on drug release mechanism studied at a preformulation stage," Journal of Controlled Release, vol. 95, pp. 101-108,(Feb. 2004).
Dixit et al., "Oral strip technology: Overview and future potential," Journal of Controlled Release, vol. 139, pp. 94-107 (2009).
International Search Report dated Sep. 12, 2015 in application No. PCT/EP2015/075697.
METHOCEL, "Chemistry of METHOCEL™ Cellulose Ethers," Dow (2013).
Nishigaki et al., "Development of fast dissolving oral film containing dexamethasone as an antiemetic medication: Clinical usefulness," International Journal of Pharmaceutics, vol. 424, pp. 12-17 (2012).
Nishigaki et al., "Development of fast dissolving oral film containing dexamethasone as an antiemetic medication: Clinical usefulness," International Journal of Pharmaceutics, vol. 424, pp. 12-17, (Dec. 2011).
Office Action in U.S. Appl. No. 15/523,502 dated Mar. 9, 2018.
Office Action in U.S. Appl. No. 15/523,502 dated Oct. 31, 2017.
Office Action in U.S. Appl. No. 15/523,502 dated Sep. 10, 2018.
Shimoda et al., "Preparation of a fast dissolving oral thin film containing dexamethasone: A possible application to antiemesis during cancer chemotherapy," European Journal of Pharmaceutics and Biopharmaceutics, vol. 73, pp. 361-365 (Sep. 2009).

* cited by examiner

*Primary Examiner* — Susan T Tran
*Assistant Examiner* — William Craigo
(74) *Attorney, Agent, or Firm* — Foley & Lardner LLP (57) ABSTRACT

The present invention relates to an oral film consisting essentially of dexamethasone and hydroxypropyl methylcellulose, wherein the concentration of dexamethasone is 30% w/w or more and the concentration of hydroxypropyl methylcellulose is between 35 and 70% w/w based on total dry matter.

17 Claims, 1 Drawing Sheet

DEXAMETHASONE ORAL FILM

CROSS-REFERENCE TO RELATED APPLICATIONS

The present application is a continuation of U.S. application Ser. No. 15/523,502, filed May 1, 2017 (now abandoned), which is the U.S. National Stage of International Application PCT/EP2015/075697, filed Nov. 4, 2015, and claims priority to Denmark Patent Application No. PA 2014 70674, filed Nov. 4, 2014.

FIELD OF THE INVENTION

The present invention relates to dexamethasone oral films, their use and a method for preparing such films. The oral film according to the invention is suitable for administration to the oral cavity where it disintegrates rapidly and gives rise to a fast rise in plasma dexamethasone concentration.

BACKGROUND OF THE INVENTION

Oral film is a dosage form which has been used for various types of drug substances including buprenorphine/naloxone (Suboxone® film against opioid dependence), odansetron (Setofilm®/Zuplenz® film against nausea), amlodipine (against hypertension), loperamide (antidiarrheal), nicotine (NiQuitin® film for smoking cessation), donepezil (against Alzheimer's) and others. It has also been used for OTC products without any active drug substances (e.g. breath fresheners, teeth whitening, cough and cold indications, bloating relief, etc.).

Dexamethasone is a well-established drug substance which has been used in medicinal products for many decades. It is used for conditions requiring anti-inflammatory or immunosuppressive actions, and for corticosteroid substitution therapy. Some examples are cerebral oedema, acute serve asthma, acute dermatological diseases, autoimmune diseases, Addison's disease, rheumatoid arthritis, croup, prophylaxis and treatment of nausea and vomiting induced by chemotherapy against cancer. Despite the introduction of various new drug classes, dexamethasone is still widely used and occurs in no less than five different categories in the WHO Model Lists of Essential Medicines. Known oral formulations of dexamethasone include conventional tablets and solutions for oral administration. However, many patients has difficulties or disturbances in eating or swallowing or are unable or unwilling to do it, for example some of the very elderly, the very young or those that are in confusion or in distress. Examples of these patients or situations can be found within for example oncology therapy, paediatrics, various community care or home care situations, palliative care, and in the emergency treatment of serious acute allergic conditions or anaphylaxis. For these, conventional tablets and solutions for oral administration are not always the ideal dosage form.

Furthermore, it is advantageous with a fast systemic absorption of the dexamethasone, for example, but not limited to, serious acute allergic conditions or anaphylaxis in particular if adrenalin is not available, or for the treatment of croup. Furthermore, there are medical emergency situations where dexamethasone is indicated but where no water is available or not readily available within a reasonable time, which could make it difficult or impossible to successfully administer dexamethasone tablets. Similarly, there are situations and circumstances where tablet jars or tablet bottles, or oral solutions bottles, cannot be easily be carried by person at risk for needing fast access to dexamethasone, due to their size or fragility. For example, at work, in cars, at school, in boats or at mountain climbing or other outdoor activities.

Thus, there is a need for developing a dexamethasone formulation for oral administration, which can be administered without any water and which does not require swallowing of a tablet or a significant volume of solution, which has a small size thus being more likely to be available when needed than if it would have been larger or more bulky, which has a fast systemic absorption, and which can be administered also to patients in distress or even to those being unconscious by medically trained or not trained that are helping the patient. It is advantageous if this film can also accommodate the higher level of doses often used for dexamethasone in many indications, which are 8 mg or above.

Shimoda et al. (Eur. J. Pharm. Biopharm. 73 (2009) 361-365) describes a fast dissolving oral thin film containing dexamethasone with a possible application to antiemesis during cancer chemotherapy. The basic materials of the film were microcrystalline cellulose (57%), polyethylene glycol (15%), hypromellose (7.4%), polysorbate 80 (5.4%), and L-HPC (1.3%). Said excipients apparently constituted approximately 86% of the formulation, which thus allows for approximately 14% of the active ingredient dexamethasone. (As known to those skilled in the art, film compositions are usually presented based on total dry weight, i.e., not considering residual water or other residual process solvents, and not considering the composition of the so called wet mass with which the manufacturing starts but from which water and other process solvents are evaporated during the process. The figures given herein thus refer to such dry weight).

These basic materials were mixed, fragrance ingredients were included and then the mixture (i.e. the wet mass) was coated onto plastic film to prepare the thin film and then dried. The resultant dry film was cut into square pieces of 2 cm×2 cm, each in which there were 4 mg of dexamethasone. The inventor described the film to be rapidly dissolving and the explanation therefore was the inclusion of high amounts of microcrystalline cellulose in the preparation (more than 50%). The pharmacokinetics of the film, including the rate of systemic dexamethasone absorption, were tested in rats and the results thereof showed a t(max) of about 3.2 hours i.e. dexamethasone reached its highest plasma concentration after 3.2 hours. t(max) is the most widely used measure of systemic absorption rate, or rate of uptake as it may also be called. It refers to the time at which C(max), the highest achieved plasma concentration, occurs.

In a later study (Nishigaki et al., International Journal of Pharmaceutics, 424 (2012) 12-17) the same film product was studied on cancer patients. Its potential usefulness as an antiemetic agent in patients receiving chemotherapy was confirmed, but the authors failed to determine t(max) or other pharmacokinetic parameters in that study. According to scientific literature and to the information supplied with marketed oral dexamethasone product, however, t(max) for humans after oral administration of dexamethasone is typically 1.5 hours.

The t(max) found by Shimoda et al. in the rat model for the film later being used in Nishigaki et al. was 3.2 hours.

Accordingly, there is a need for developing an oral dexamethasone film which more rapidly reaches t(max) than was the case for the film developed by Shimoda et al. Moreover, in many treatment situations, where dexamethasone is indicated, the single dose is higher than 4 mg, and often being 8 mg or even higher. Thus, there is also a need for developing a dexamethasone film which has a higher dose than 4 mg in each unit but not at the expense of a film size that is two times larger or even four or six times larger than the 4 mg film developed by Shimoda et al. (which was 2 cm×2 cm), because a film twice or more that size would diminish some of the advantages and convenience with using the film as dosage form.

DETAILED DESCRIPTION OF THE INVENTION

The present invention provides an oral film consisting essentially of dexamethasone and hydroxypropyl methylcellulose (hypromellose), wherein the concentration of dexamethasone is 30% w/w or more and the concentration of hydroxypropyl methylcellulose is between 35 and 70% w/w based on dry matter.

In the present context the term "consisting essentially of" means that the main ingredients are dexamethasone and hydroxypropyl methylcellulose, but a minor concentration of excipients/additives is acceptable. Thus, up to in total 5% w/w of excipients/additives may be present in the composition. This means, that eg taste-masking agents, sweetening agents, aroma-giving agents, flavouring agents, pharmaceutically acceptable excipients may be present in the oral film, but the total concentration of such substances is max. 5% w/w based on the total weight of the oral film. As seen from the examples herein a suitable oral film can be made only based on dexamethasone and hydroxypropyl methylcellulose.

As described in the examples herein an oral film according to the invention is easy to handle, is not hygroscopic, has excellent stability, does not have a high bio-adhesivity, disintegrates fast, releases dexamethasone fast, and results from a clinical study show that it is safe, tolerable and achieves a systemic absorption of dexamethasone that is equal of faster than what has been reported in the literature for oral dexamethasone tablets.

There are various subcategories and various words for oral films, for example, buccal film, sublingual film, bioadhesive film, transmucosal film, orodispersible film and oral dissolvable film. To some extent these different words indicates different administration sites or mechanisms of action, but the terminology is not always distinct or mutually excluding, For example, a buccal film may be bioadhesive and may give rise to transmucosal absorption and gastrointestinal absorption of the active substance in parallel.

In the present context the term "oral film" is intended to denote a water soluble film that is administered to the oral cavity and from which a systemic absorption takes place and said absorption to a significant extent takes place in the gastro-intestinal tract. Moreover, dexamethasone is present in the invention in solid form, i.e. micronized particles being dispersed in the polymer matrix. In general it is believed that substances that are sparingly soluble in water, such as dexamethasone, preferably should be present in dissolved form in the dosage form, in order to enable a fast dissolution and subsequent fast systemic absorption. However, the present inventor has surprisingly found that although dexamethasone is present in solid form in the invented film, a suitable and fast systemic absorption is obtained after oral administration despite the fact that no water was given to the human subjects during the administration. This has made it possible to avoid using excipients that are otherwise often employed to improve dissolution rates, disintegration rates and/or absorption rates, such as the microcrystalline cellulose as proposed by Shimoda et al, or polyethylene glycol or polysorbate 80. If it can be avoided, as in the case of the present invention, to use such excipients it becomes possible to have a relatively high load of dexamethasone in the film so that a unit dosage of a suitable size can be administered and at the same time provides a dose that may be higher than the 4 mg dose proposed by Shimoda et al.

Furthermore, another limiting factor for a high drug load, when dexamethasone is dissolved in the polymer matrix (rather than being dispersed as micronized particles in the polymer matrix as is the case for the current invention) is that the solubility of dexamethasone in the polymer matrix is limited, which means that if the dexamethasone concentration is above a certain level the dexamethasone may precipitate and such precipitate may not only be amorphous or having unknown and potentially disadvantageous crystalline forms than the original but it may also introduce a general gradual change in product quality and appearance as storage time progress. One may also expect that not just that physical stability but also the chemical stability will be better when the dexamethasone is dispersed as particles than when molecularly dissolved.

There are thus both a drug load factor and a stability factor that speak in favour for letting the dexamethasone be present in the film as micronized particles dispersed in the polymer matrix, provided however that a composition can be identified that allows a fast disintegration of the film and subsequent fast dissolution of the admittedly sparingly soluble dexamethasone. The present invention overcomes that challenge.

An oral film according to the present invention is a very thin film and is suitable to administer to the oral cavity, where it disintegrates very fast and the allowing the dexamethasone to dissolve and being swallowed with the saliva present in the mouth and subsequently being systemically absorbed predominately via the gastrointestinal route.

Initially it was however believed that dexamethasone would largely be systemically absorbed via the oral mucosa (so called transmucosal absorption) and, accordingly, that it was important that the film could adhere to the oral mucosa to allow for direct contact and transfer of dexamethasone to and through the mucosa. However, the present inventor has realised, by conducting and correctly interpreting in vitro and in vivo experiments, that dexamethasone is not absorbed through the oral mucosa in an amount that makes it therapeutically effective. Accordingly, the task has been to develop a formulation that at least has the same or better extent and rate of systemic absorption as marketed dexamethasone tablets and, moreover, that the formulation should enable a higher drug load than 4 mg yet not being 4 cm×4 cm or larger, and that it should be possible to administer the formulation without any water and without any assistance of medical personnel.

The latter is especially important in acute allergic reactions or anaphylactic shock, where the patient may be in distress or even unconscious and administration of a conventional dexamethasone tablet or oral dexamethasone solutions is not easily made.

During the development work the present inventor realised that mucoadhesive films, when placed in sublingual or buccal positions, did not achieve an acceptable rate and extent of systemic dexamethasone absorption, and that the addition of solubility enhancers such as polysorbate 80 did not improve this situation. However, the inventor also observed that a suitable disintegration and dissolution, and subsequent systemic uptake, could be obtained by using a mix of two or more HPMC qualities.

Even if the inventor arrived at a very plain formulation which contains just one type of excipient, i.e. HPMC, it is possible to include minor amounts of functional excipients, for example taste-masking additives or additives that give an opaque and/or colored appearance to the film. To avoid interfering with the desirable fast systemic absorption, or with the high drug load, such additives should however maximally constitute in total 5% w/w of the total dry matter of the film.

The finished dried film product based on the current invention may contain 0-10% w/w, notably 2-5% w/w, residual water. However, the concentrations given above relating to content of dexamethasone, HPMC and other excipients/additives, are based on the weight of the total dry matter in the composition (i.e. possible content of residual water is excluded). As known to those skilled in the art, film compositions are usually presented based on total dry weight, i.e., not considering such residual water or other residual process solvents, and not considering the composition of the so called wet mass with which the manufacturing starts.

Examples of suitable compositions are given in the examples herein. In such films the sum of the concentrations of dexamethasone and hydroxypropyl methylcellulose (HPMC) based on the total dry weight is from 95% to 100% w/w. In a particular example the sum is 100% w/w, i.e. no other excipients are present.

As observed by the inventor, the film according to the invention does not need to be bioadhesive or mucoadhesive as it is preferably placed on the tongue and rapidly disintegrates and dissolves.

Hydroxypropyl methylcellulose (HPMC) is the film-forming excipient in the present invention. Suitable grades of HPMC and possible other film-forming agents for use in an oral film according to the invention are described below. The concentration of HPMC(s) in an oral film is normally in a range of from 35 to 70% w/w. The total concentration of HPMCs may be from about 40 to about 70% w/w, from about 45 to about 70% w/w or from about 50 to 70% w/w. As seen from the examples herein the range may be from 55 to 65% w/w, notably about 60% w/w. The % w/w are given based on total dry matter in the oral film.

In short, the HPMC for use in an oral film according to the invention may be as specified in Ph. Eur., it may be type 2910 and/or it may be a mixture of two or more HPMCs having different viscosities. In the latter case, the concentrations in the film of the two or more HPMCs having different viscosity may be the same or different, notably the same. As seen from the examples herein, where two HPMCs are present in an oral film the concentration of the first HPMC may be from 25-50% w/w and the concentration of the second HPMC may be from 10-45% w/w and the sum concentration of the two HPMCs is from 35-70% w/w. In the case that more HPMCs are present in an oral film, the individual concentration may span over the range 10-50% w/w of each HPMC and the sum concentration of all HPMCs is from 35-70% w/w.

Moreover, in such situations where there is a mixture of two HPMCs these HPMCs may have a viscosity of 3 mPa s and 50 mPa s, respectively.

As it appears from the examples herein an oral film according to the present invention may contain a mixture of HPMCs having a viscosity of 3 mPa s and 50 mPa s, respectively. The total concentration of HPMCs may be as described above. In specific films the individual concentrations of HPMC 3 mPa s and HPMC 50 mPa s are the same such as, eg, in a range of from 20% w/w to 35% w/w for each HPMC and based on total dry matter in the oral film. As seen from the examples herein films with suitable properties are obtained for a film according to the invention that contains a mixture of HPMCs having a viscosity of 3 mPa s and 50 mPa s, respectively, and a total concentration of HPMC s of 60% w/w (based on total dry matter).

In order to obtain a strength of each film unit that corresponds to 8 mg which is not an unusual dose for many acute or serious conditions, the concentration of dexamethasone ("drug load") in the film must be relatively high. Thus, an oral film according to the present invention normally has a concentration of dexamethasone from approximately 35 to 45% w/w, based on the total dry weight of the film. In some cases, the concentration of dexamethasone is approximately 40% w/w, and in some cases even higher.

As mentioned herein below, dexamethasone is present in solid form in the polymer matrix making up the oral film. The small size of such dexamethasone particles is also an advantage with respect to obtaining a desired fast dissolution of the drug substance. It is contemplated and generally assumed that the manufacturing method does not affect the particle size of dexamethasone because the process solvent used is water, dexamethasone has limited water solubility and the water is evaporated during the process.

The oral film must have a suitable small thickness, which is a challenge when the drug load is relatively high. The thickness is important as it contributes to fast disintegration of the film and the subsequent dissolution and systemic absorption. Normally, oral films may have thickness up to 50 μm or even up to 100 μm but it is thus preferable with a thinner film, such as 15 μm or up to 30 μm. In one example the current invention has a thickness of about 25 μm. Thickness of films can be measured with various methods (e.g., manual micrometers, laser devices, etc.) but the preferred way when doing manufacturing and quality control of films is to not measure the thickness as such but rather measure the so called area weight, e.g. grams of wet or dry film per square meter, which adequately reflects the thickness because the density is rather constant and approximately 1.1-1.3 gram per cubic centimeter. For example, a thickness of 25 μm may correspond to an area weight of about 30 grams per square meter.

In the present context the term "oral film" is intended to mean both a film layer (bulk product) as it appears after drying but also to mean the cut-out pieces of the film layer. The latter can also be called film units. One film unit contains the desired and precise amount of dexamethasone, e.g. 8 mg, so it is typically regarded as a unit dosage form. As discussed later herein, the unit dose may vary, but one of the advantages with the oral film in the current invention is that it can be designed to contain 8 mg dexamethasone per unit and more such as 8 mg per unit or 16 mg or even 24 mg per unit, although high doses such as 10 mg per unit and above may not allow film as thin as 25 μm. Typically it contains 8 mg dexamethasone per unit, but the amount may vary dependent of the thickness of the film and the area size of the film unit. In general a film unit contains from 4 to 10 mg of dexamethasone.

A film unit of the current invention is typically administered to the oral cavity by placing it on the tongue. As discussed herein, it is not intended to adhere to the tongue or other oral mucosa, but rather to disintegrate fast and thus allowing for dissolution of dexamethasone and the subsequent systemic absorption is envisaged to predominately take place via the gastrointestinal route which—in the case of dexamethasone—is not a very slow route and does not suffer from severe first pass effects. However, a certain degree of bioadhesion is at hand for a short period of time before disintegration takes place as can be expected when placing a dry hydrophilic material to a moist mucosa.

With disintegration is meant the disintegration of the film unit (i.e. polymer matrix degrades into smaller segments or dissolves) whereas the term dissolution refers to the dissolution of the dexamethasone particles, said dissolution taking place both during and after the disintegration of the film unit.

Dexamethasone

Dexamethasone is a white or almost white, crystalline powder. It is practically insoluble in water and sparingly soluble in anhydrous ethanol.

In cases where increased drug solubility is desired, e.g. injectables or oral solutions, sometimes the water soluble prodrug dexamethasone sodium phosphate is used instead of dexamethasone. Dexamethasone sodium phosphate shows a fast and complete conversion to dexamethasone after administration and is generally regarded as medically equivalent to dexamethasone. There are also other derivatives or pro-drugs of dexamethasone, most of which are less widely used than dexamethasone and dexamethasone sodium phosphate and some of which do not occur in any marketed or approved medicinal products at all. When referring to "dexamethasone" in this patent application, dexamethasone sodium phosphate is also included. However dexamethasone sodium phosphate is extremely hygroscopic and is freely soluble in water and if dexamethasone sodium phosphate is used some or all of the substance may be dissolved in the film which may be a disadvantage for product performance but the amount incorporated into the film should in any case be equivalent to a molar basis to that of dexamethasone. Due to the hygroscopicity and water solubility of the dexamethasone sodium phosphate, as well as other reasons, it is preferred to employ dexamethasone in a film of the present invention.

In a film of the present invention, dexamethasone is present in solid form and more specifically it is incorporated into the film manufacturing in micronized form. Thus, dexamethasone is used in micronized form which is determined by volume:

≥80% of the particles have a size of ≤5 μm,
≥99% of the particles have a size of ≤15 μm, and
100% of the particles have a size of ≤30 μm, or
or is determined by numbers:
≥90% of the particles have a size of ≤5 μm, and
100% of the particles have a size of ≤15 μm.

It is contemplated and generally assumed that the particle size of dexamethasone in the finished film is the same or almost the same as the particle size of the micronized substance added in the manufacturing (i.e. the size distributions mentioned above) albeit this is rarely subject to measurements and is not specified in product specifications.

The concentration of dexamethasone in the film is 30% w/w or more such as from 30% to 65% w/w. As seen from the examples herein suitable a concentration range is also from 35% to 45% w/w, notably about 40% w/w.

Hydroxypropyl Methylcellulose (HPMC, Hypromellose)

The excipient hydroxypropyl methylcellulose (HPMC) has been found suitable as a film forming agent in the present invention. Examples of HPMCs are Metolose-60-SH-15, Metolose-60-SH-50, Metolose-60-SH-10000, Metolose-65-SH-50, Metolose-65-SH400, Metolose-65-SH-1500, Metolose-90-SH-400, Metolose-90-SH-4000, Metolose-90-SH-15000, Metolose-90-SH-100000, and Pharmacoat 606, and a manufacturer and supplier thereof is Shin-Etsu Chemical Co., Ltd, Tokyo, Japan. These different qualities of HPMC differ with regard to viscosity.

As shown in examples below, mixtures of two qualities of HPMC may be selected to attain rapid disintegration of the film followed by dissolution and rapid systemic absorption of dexamethasone in the plasma. For example, suitable results are obtained using a mixture of one HPMC having a viscosity of 3 mPa s and another having a viscosity of 50 mPa s.

Hydroxypropyl methylcellulose (HPMC) is also denoted hypromellose (USP) or hypromellosum (Ph. Eur.). The chemical name is cellulose, 2-hydroxyropyl methyl ether (CAS 9004-65-3). Dependent on the substitution pattern HPMC is also divided into different types:

| Type | Methoxy content JP 2001 | Methoxy content USP 25 | Hydroxy-propoxy content JP 2001 | Hydroxy-propoxy content USP 25 |
|---|---|---|---|---|
| Type 1828 |  | 16.5-20.0% |  | 23.0-32.0% |
| Type 2208 | 19.0-24.0% | 19.0-24.0% | 4.0-12.0% | 4.0-12.0% |
| Type 2906 | 27.0-30.0% | 27.0-30.0% | 4.0-7.5% | 4.0-7.5% |
| Type 2910 | 28.0-30.0% | 28.0-30.0% | 7.0-12.0% | 7.0-12.0% |

Moreover, the individual types are available in many different viscosity types. More details regarding HPMC and regarding measuring the viscosity of HPMC is given in Handbook of Pharmaceutical Excipients, 4$^{th}$ Edition, PhP Press, 2003, i.e. measuring a 2% w/v aqueous solution at 20° C.

An interesting result reported in the examples herein is where type 2910 with a viscosity of 3 mPa s and 50 mPa s, respectively, has been employed. A person skilled in the art can, based on the examples given herein, perform the necessary adjustments in order to use other combinations of HPMC and/or other cellulose derivatives as mentioned below, especially in view of the results given herein. Care should be taken to obtain the desired result; as seen from the comparative examples herein even minor changes may lead to an unwanted result. The aim should be to achieve a film that, although very thin, has an acceptable mechanical strength, can be bended without breaking and not being very brittle, but still have a high disintegration rate as explained above and the subsequent high systemic absorption rates.

Thus, an oral film of the present invention contains HPMC and that HPMC may be in the form of a mixture of two or more HPMCs having different properties such as being of different substitution types or having different viscosities. As seen from the examples herein an oral film according to the present invention may contain a mixture of two HPMCs with the same substitution pattern (e.g., Type 2910) but where one has a higher viscosity and the other.

The total concentration of HPMC(s) in an oral film of the invention may be in the range from 35 to 70% w/w, from 40 to 70% w/w, from 50 to 70% w/w, or from 55 to 65% w/w. In a particularly interesting example, the total concentration of HPMC(s) in the film is about 60% w/w.

Other Possible Substituents for Hydroxypropyl Methylcellulose or Additives

Hydroxypropyl methylcellulose may be replaced with another cellulose derivative such as methyl cellulose, hydroxyethyl cellulose (HEC), hydroxypropyl cellulose (HPC), ethyl hydroxyethyl cellulose, carboxymethyl cellulose, carboxymethyl cellulose including sodium carboxymethyl cellulose, and microcrystalline cellulose, and mixtures thereof.

However, the final film formulation must have the same or very similar properties regarding handling, disintegration, dissolution, systemic dexamethasone absorption, therapeutic effect, fast onset of action, stability and drug load as the film formulations exemplified in the examples herein.

Examples of methylcelluloses (MC) are Metolose SM-4 (MC1), Metolose SM-15 (MC2), Metolose SM-100 (MC3), Metolose SM-400 (MC4), Metolose SM-1500 (MC5), Metolose SM-4000 (MC6), from Shin-Etsu, Japan. Examples of sodium carboxymethylcellulose (CMC) are Low viscosity CMC (CMC1), Medium viscosity CMC (CMC2), High viscosity CMC (CMC3), supplied by Sigma-Aldrich, St. Louis, USA. An example of hydroxyethylcellulose (HEC) is Natrosol 250 HX, supplied by Hercules, Wilmington, USA.

A Method for Preparing an Oral Film According to the Invention

The invention also provides a method for preparing an oral film of the present invention, the method comprises the steps of:
i) dissolving the hydroxypropyl methylcellulose excipients in water to obtain a viscous solution,
ii) dispersing micronized dexamethasone in said solution,
iii) coating the viscous wet mass resulting from step ii) on an intermediate liner and adjusting the thickness of the wet mass layer with a micrometer adjusted knife to obtain a wet film of suitable and even thickness,
iv) drying the wet film, and
v) removing the intermediate layer during or before cutting the now dry film into suitable sizes for subsequent packaging into feasible pouches or other primary containers.

Alternatively, step (ii) may be to prepare an aqueous dispersion of the micronized dexamethasone and then mix that with the viscous polymer solution obtained in step (i) or even change the order of said step (i) and (ii). In any case, the aim is to achieve a homogenous wet mass for use in step (iii).

Use of an Oral Film According to the Invention

As mentioned herein, dexamethasone is an established drug substance, which has been used in medicinal products for decades. It has anti-inflammatory and immunosuppressant effects and is used to treat inflammatory and autoimmune conditions such as rheumatoid arthritis, bronchospasm, and idiopathic thrombocytopenic purpura. It is also used to counteract allergic reactions or anaphylactic shocks, and to treat plantar fascilitis and in eye surgery. It is also used in patients undergoing chemotherapy to counteract side effects of that anti-tumor treatment. Thus it can augment the antiemetic effect and counteract the development of oedema. It may also be used as a therapeutic agent itself in certain haematological malignancies such as multiple myeloma. Another application is croup in children. Dexamethasone may also be used to treat adrenal insufficiency, Addison's disease or in congenital adrenal hyperplasia, or it may be used in the treatment of high altitude cerebral oedema as well as pulmonary oedema.

Specifically, a film according to the invention is suitable for use in the treatment of chemotherapy induced nausea and vomiting, croup, acute allergic reactions, anphylactic conditions, brain oedema or high-altitude disease.

An oral film of the present invention may be used for any of the diseases mentioned above. In particular it may be used in situations where a fast onset of action is desired. In the present context a fast onset of action is intended to mean that tmax is reached equally fast or faster than the typical 1.5 hours commonly reported in the literature for oral dexamethasone. Following such systemic availability of dexamethasone, the actual onset of pharmacological action depends on the mechanisms of action of dexamethasone which may be different for different diseases and conditions but it is clearly always the case that the desirable effects occurs faster if the systemic absorption is fast than if it is slow.

Another preferred and suitable use of the present invention is for patient groups which due to the disease or condition being treated (e.g. cancer, acute allergy, croup, etc.) or due to other reason (very young or very old, general weakness, mental disabilities, etc.) have difficulties swallowing or difficulties self-administrating a medication.

The dose should be adjusted dependent on the particular disease, severity of the disease and the patient's condition, age and weight. Normally the initial dose is from between 0.5 to 8 mg per day, but daily doses higher than 8 mg may be required.

For example, the dose should be from 4 to 16 mg daily or from 2 to 8 mg daily in the treatment of cerebral edema (e.g. in connection with brain tumors) and from 8 to 16 mg or from 4 to 12 mg daily in the treatment of cancer mammae, ovarii, prostatae or testis. To prevent nausea or vomiting in connection with chemotherapeutic treatment the dose is normally from 8 to 12 mg daily, which increases to from 16 to 24 mg daily.

Dexamethasone tablets typically contain 1 or 4 mg dexamethasone, although 6 and 8 mg tablets may sometimes be available in some countries. Thus, if a daily oral dose of 24 mg is required, 24 tablets of 1 mg or 6 tablets of 4 mg must be administered to the patient, said patient having a likelihood of having difficulties in swallowing tablets due to either the disease or basic treatment of the disease. This also indicates the need for developing an improved and patient friendly formulation having a higher strength than 1 or 4 mg. Accordingly, another preferred application of the invention is when rapid and easy administration of 8 mg or higher is needed and no similar easy-to-use dexamethasone products of suitable strengths are available. Yet another advantage is realized when no drinking water is available.

BRIEF DESCRIPTION OF THE DRAWINGS

FIGS. 1A and 1B shows the results of the pharmacokinetic study reported in Example 4 herein. It shows the average plasma concentration vs time curve for N=30 human study subjects after administration of an oral film according to the present invention or dexamethasone tablets, using a cross-over study design.

The invention is further illustrated in the following examples, which are for illustrative purposes and they are not intended to limit the invention.

Methods and Materials

Micronized Dexamethasone

Micronized dexamethasone, Ph. Eur. were obtained from Sanofi Chimie, France it is determined in volume as:
  ≥80% of the particles have a size of ≤5 μm,
  ≥99% of the particles have a size of ≤15 μm, and
  100% of the particles have a size of ≤30 μm,
or determined in number as:
  ≥90% of the particles have a size of ≤5 μm, and
  100% of the particles have a size of ≤15 μm.

Other Excipients and Materials

Hypromellose type 2910 3 mPa s, PhEur (Pharmacoat 603) and Hypromellose type 2910 50 mPa s, PhEur (Metolose-60-SH-50) were obtained from Shin-Etsu, Tokyo, Japan.

PET (polyethylene terephthalate) liner, a typical inert coating material complying with the applicable requirements of the EU "framework regulation" for food contact materials, 1935/2004, was used as intermediate liner and was purchased from Loparex Group.

Comparator Product for Human PK Study

Fortecortin tablets 4 mg dexamethasone, a conventional dexamethasone tablet marketed in Spain by Merck, S. L, Maria de Molina, Madrid Spain, batch number M1337 09/2015, were purchased in a Spanish pharmacy.

Manufacturing Equipment for Manually Made Lab Scale Batches

The coating equipment used was a manual coating line using a motor driven coating knife to coat the coating mass on a technical film (e.g. Coatmaster 510) and was supplied by Erichsen. Such film knifes are also available from for example Sheen Instruments.

The drying equipment used was a static drying oven (e.g. Heraeus UT6120) and was supplied by Heraeus.

Die cutting equipment used was a manual die cutting machine comprised of a basic die cutting machine and a die cutting tool (6.6 cm$^2$) and was supplied by Fritschi and Marbach.

For large scale manufacturing in a continuous rather than batch wise fashion, other equipment will be used.

Assay for Dexamethasone and Related Substances

The assay and related substances are determined simultaneously by HPLC. A Waters Xterra RP8 analytical column (100×4.6 mm, 3.5 µm) is used with a mobile phase composed of water/acetonitrile (76/24) at a flow rate of 1.5 mL/min. The column effluent is monitored at a wavelength of 240 nm. The samples are dissolved in diluent (water/acetonitrile 72/28) and injected for analysis. A run time of about 32 min is used to elute dexamethasone and monitor the related substances. Quantification of dexamethasone is performed by means of external calibration using Dexamethasone, USP reference standard or Dexamethasone, USP drug substance. The average of 3 samples each of 4 pooled strips is calculated and the assay result is reported as mg/strip. Other peaks (excluding peaks found in the diluent) are reported as related substances by identity or relative retention time (unknown) in area % of the main peak. The reporting threshold is 0.1%. The sum of all reported impurities (above 0.1% peak area) is reported as "total impurities". The HPLC procedure described above is also used for the identity test. The retention times of the dexamethasone peak in the sample and standard solution are compared. Also the spectra of the major peak in the sample and standard chromatograms are obtained and compared for similarity.

Dissolution Testing

A dissolution medium of 0.2% aqueous sodium lauryl sulphate is used. Six strips are tested. A sample is withdrawn from the dissolution medium after 10 minutes, and dexamethasone quantified by UV/vis absorption spectroscopy. The average, highest, and lowest values are reported as percent of label claim. The method is performed as described in the USP <711> Dissolution, Apparatus 2 using the alternative sinkers. It is harmonized with Ph. Eur. 2.9.3, Apparatus 2 except for the national USP text.

Bioanalysis for Determination of Dexamethasone in Human Plasma

The analysis was performed using ultra performance liquid chromatography coupled to tandem mass spectrometry (UPLC-MS/MS) running in the Multiple Reaction Monitoring (MRM) mode. The calibration was carried out using an isotopically labelled internal standard (dexamethasone-d4). The bioanalysis was performed using dexamethasone (lot #3-QL-138-1) obtained from Toronto Research Chemicals (North York, ON, Canada) as the calibrant and tetradeuterated dexamethasone (2H4-dexamethasone=dexamethasone-d4) (lot #R420P101) obtained from C/D/N Isotopes (Pointe-Claire, QC, Canada) as the internal standard. The chemicals used for sample preparation and mobile phases were obtained commercially and were of analytical grade or better. Water was purified in a Millipore® water purification system (Millipore, Bedford, USA). The K2EDTA plasma used for preparation of calibrators and quality control (QC) samples (lot #3C0406 and lot #3D0590) was purchased from 3H Biomedical, Uppsala, Sweden. The instrumentation consisted of an Acquity UPLC pump coupled to a Quattro Ultima Pt tandem quadrupole mass spectrometer (Waters Corp., Milford, Mass., USA). The ionisation technique was positive electrospray. The chromatographic column was a Waters BEH C18 (100×2.1 mm length×inner diameter, particle diameter 1.7 µm). In brief the procedures of this method were as follows. To the plasma samples (500 µL), 50 µL of milliQ-water and 50 µL of internal standard solution (dexamethasone-d4 5.0 ng/mL in water/methanol (1:1 v/v)) were added. Liquid-liquid extraction was then performed to 2.0 mL of dichloromethane. The samples were vortex mixed and centrifuged at 3500 g for 10 minutes at room temperature in a Hereaus centrifuge. The samples were then reconstituted in 125 µL of 0.1% formic acid in milliQ/methanol (1:1 v/v) where after they were vortex mixed for 5 min and transferred to vials for injection into the UPLC-MS/MS system. The chromatographic elution was carried out with a mobile phase consisting of the components A: 0.2 mM ammonium formate buffer with 0.05% formic acid (pH 2.8) and B: acetonitrile delivered as the following gradient program: 0-4.7 min 23% B; 4.7-4.8 min 23-90% B; 4.8-5.8 min 90% B; 5.8-5.9 min 90-23% B; 5.9-6.8 min 23% B. The total run time was 6.8 min. The flow-rate was 0.65 mL/min and the column temperature was set at 65° C. The injection volume was 10 µL. The cone voltage was 50 V and the collision energy was 14 eV for the analyte and the internal standard. The collision gas was argon. The data collection was made in Multiple Reaction Monitoring (MRM) mode. The MRM transitions used were: m/z 373→355 for dexamethasone [M+H]+ and m/z 377→359 for the internal standard. The retention times for the analyte and the internal standard were both about 4.2 min. The integration of the chromatographic peaks and the calculations were carried out using the software MassLynx v. 4.1 SCN627 (Waters Corp., Milford, Mass., USA). The chromatographic peak area ratios (analyte/internal standard) were plotted as a function of analyte concentration (ng/mL plasma). Linear regression with the weighting factor $1/x^2$ was used for curve fitting of the results from the calibration samples. The resulting functions had the format y=kx+m, where y is the peak area ratio, k is the slope, x is the concentration (ng/mL) and m is the intercept. The quantitative values (x ng/mL) in the unknown samples, the calibrators (back-calculation) and QC samples were calculated as x=(y−m)/k.

Bioanalysis for Determination of Dexamethasone in Syrian Hamster Plasma

Quantitative determination of dexamethasone in hamster plasma used liquid chromatography coupled to tandem mass spectrometry (UPLC-MS/MS). The analytical principle was: The sample preparation of the plasma was performed by liquid-liquid extraction, isolation and evaporation of the organic phase followed by reconstitution of the sample. The analysis was carried out by UPLC-MS/MS with positive electrospray ionization. The data acquisition mode was Multiple Reaction Monitoring (MRM). The calibration was made by the chromatographic peak area ratio (analyte/internal standard 2H4-dexamethasone) as a function of dexamethasone concentration. Hamster blank plasma was supplied by CiToxLAB. Chemicals used were: 2H4-dexamethsone, Water purified in a milliQ Purification System, Methanol, Dichloromethane, Formic acid and Ammonium formate. UPLC-MS/MS equipment was Waters Acquity UPLC with Column: Acquity UPLC BEH C18 (100×2.1 mm, 1.7 μm) with Column temperature: 65 C, Injection volume: 10 microL, Mobile phase: A: 0.2 mM ammonium formate+0.05% formic acid (aq), B: methanol. Flow-rate: 0.4 mL/min Run time: 5.8 minutes. LLOQ for dexamethasone in hamster plasma was estimated to 20 ng/mL.

EXAMPLES

Example 1. Preparation of Oral Film Containing Dexamethasone According to the Invention Batch Formula:

| | | |
|---|---|---|
| Dexamethasone, PhEur | 68 g | (40% w/w of dry weight) |
| Hypromellose type 2910 3 mPa s, PhEur | 51 g | (30% w/w of dry weight) |
| Hypromellose type 2910 50 mPa s, PhEur | 51 g | (30% w/w of dry weight) |
| Water purified | 830 g | |

The oral film of dexamethasone consists of dexamethasone and hypromellose type 2910. An example batch formula corresponding to 170 g dry mass is listed above.

The film is prepared by adding the purified water to a suitable container. The water is heated to about 75° C. and the celluloses are added and dispersed. The heat is turned of and under stirring the coating mass is cooled to room temperature. Then dexamethasone is added and the coating mass is stirred until a homogeneous coating mass is achieved. The resulting mixture is a viscous suspension, which is then casted onto an intermediate liner made of PET with the suitable coating equipment to obtain a thin wet film resting on the intermediate liner. The thickness of this wet film layer is adjusted with a micrometer adjusted knife to obtain a wet film of suitable and even thickness. Room temperature is used for all these steps.

The wet film is then dried in a suitable drying oven with low circulation of air at an elevated temperature of 65-75° C. to evaporate the water. The temperature is critical; if too high the product may be damaged resulting in inferior mechanical quality or decreased dexamethasone stability, and if too low the desired drying will not be achieved in reasonable time.

When drying is complete, which is judged by in process controls of area weight and/or water content of the dry film, a laminate consisting of a dry film resting on the intermediate layer is obtained.

By using a die-cutter units of defined size are cut out of the laminate. Then the film is separated from the laminate and the units are inserted into pre-fabricated pouches. The pouches are sealed using a heat-sealing apparatus. The pouch is typically one which provides a barrier to moisture, light and oxygen. A suitable pouch is a polyacrylonitrile-aluminium-paper laminate pouch (Barex®).

The thickness of the film may be varied as well as the size of each unit dependent on which unit dose of dexamethasone is desirable. However, within a batch these parameters should be well defined and homogeneous.

Typically, the thickness of the film in the present invention is about 25 μm and has an area weight of about 30 g per square meter. Each unit cut from the film typically has a size of about 20×33 mm and weigh about 20 mg and each unit contains 8 mg of dexamethasone. In the film the dexamethasone is present in undissolved form i.e. same form as added. Thus, the concentration of dexamethasone/cm$^2$ is 1.21 mg/cm$^2$.

Example 2. Characteristics and Stability of a Film Containing Dexamethasone According to the Invention Units prepared as described in Example 1 and with the composition there described, but cut by hand in round-shaped forms, were subject to stability testing which also include testing at zero time i.e. soon after manufacturing. Each unit had about 3% residual moisture and contained 8 mg dexamethasone. The round-shaped films were packaged in pouches made of a laminate of Barex type (PET-aluminium-PAN (Barex®)).

The effect of temperature and humidity was studied after storage through six months for 25° C./60% RH and 40° C./75% RH storage conditions. The results from the temperature and humidity study revealed that the drug product is chemically and physically stable. Test results met the specifications under all tested conditions of temperature and humidity.

Physical Characteristics

The physical stability of the product was evaluated by assessing its appearance, water content and dissolution.

The specifications of the appearance of the product was: white to pale yellow, opaque to semi-translucent, round film, and this specification was met throughout all timepoints of the stability study.

The water content results showed no significant changes over the six month for samples stored at 25° C./60% RH. For samples stored at 40° C./75% RH conditions the testing was not done at six months. The results are shown in the table below.

Water Content Results:

| Time point | 25° C./60% RH (as % w/w) Range; Average; % RSD | 40° C./75% RH (as % w/w) Range; Average; % RSD |
|---|---|---|
| Initial | 2.72-2.96; 2.8; 4.7 | (same as 25/60) |
| 3 months | 3.41-3.68; 3.5; 3.3 | 3.93-4.03; 4.0; NA |
| 6 months | 2.94-3.05; 3.0; 1.7 | Not tested |

The dissolution of the film was evaluated at a single time point of 10 min. The results are shown in the table below.

Dissolution Test Results:

| Time point | 25° C./60% RH (% dissolved) Range; Average; % RSD | 40° C./75% RH (% dissolved) Range; Average; % RSD |
|---|---|---|
| Initial | 99-107; 103; 3.8 | (same as 25/60) |
| 1 month | 102-103; 103; 0.5 | 104-108; 106; 1.6 |
| 2 months | 104-109; 107; 2.0 | 102-108; 105; 2.4 |
| 3 months | 98-102; 100; 1.4 | 103-105; 104; 0.9 |
| 6 months | 97-106; 99; 3.8 | 104-108; 105; 1.4 |

All samples through six months at ambient initial, 25° C./60% RH and 40° C./75% RH storage conditions were above Q=80% at 10 minutes (which was the specification), i.e. at least 80% w/w of the dexamethasone is released from the dexamethasone ODF 10 minutes after start of the test.

Assay and Impurities

The content of dexamethasone and impurities were tested in triplicate and the average results are presented in the following tables. The specification of the product's assay was 7.2-8.8 mg (90.0-110.0% of LC), and this specification was met throughout all timepoints of the stability study.

Dexamethasone Assay Results:

| Time point | 25° C./60% RH Average % LC; % RSD; [Average mg/film] | 40° C./75% RH Average % LC; % RSD; [Average mg/film] |
| --- | --- | --- |
| Initial | 103.6; 0.8; [8.3] | (same as 25/60) |
| 1 month | 103.5; 1.7; [8.3] | 106.1; 1.3; [8.5] |
| 2 months | 101.8; 0.6; [8.1] | 105.4; 0.5; [8.4] |
| 3 months | 101.5; 1.0; [8.1] | 104.6; 0.3; [8.4] |
| 6 months | 105.6; 1.4; [8.4] | 103.7; 0.7; [8.3] |

Normalized Dexamethasone Assay Results (Weight Corrected):

| Time point | 25° C./60% RH Average % LC; % RSD; [Average mg/film] | 40° C./75% RH Average % LC; % RSD; [Average mg/film] |
| --- | --- | --- |
| Initial | 102.8; 0.3; [8.2] | (same as 25/60) |
| 1 month | 103.3; 0.0; [8.3] | 104.2; 0.2; [8.3] |
| 2 months | 103.2; 0.2; [8.3] | 102.1; 0.6; [8.2] |
| 3 months | 103.1; 0.1; [8.2] | 102.0; 0.5; [8.2] |
| 6 months | 102.6; 0.3; [8.2] | 101.8; 0.2; [8.1] |

Impurities Results:

| Time point | 25° C./60% RH Average Unknown; Average Total IMP | 40° C./75% RH Average Unknown; Average Total IMP |
| --- | --- | --- |
| Initial | 0.14; 0.14 | (same as 25/60) |
| 1 month | 0.13; 0.13; | 0.13; 0.13; |
| 2 months | 0.18; 0.18; | 0.17; 0.17; |
| 3 months | 0.18; 0.18; | 0.19; 0.19; |
| 6 months | 0.15; 0.15; | 0.15; 0.15; |

The results show that the product according to the invention is stable and no significant changes are observed in the assay. Moreover, no increase in degradation products is observed.

Example 3. Characteristics and Stability of an Oral Film Containing Dexamethasone According to the Invention Manufactured According to cGMP Samples prepared as described in Example 1, and with the composition there described, and according to cGMP, were subject to stability testing. Samples from the same batch were also used in Example 4.

Each unit was about 20×33 mm and aimed at 8 mg dexamethasone content. The films were packaged in pouches made of a laminate of Barex type (PET-aluminium-PAN (Barex®).

The effect of temperature and humidity was studied after storage through six months for 25° C./60% RH and 40° C./75% RH storage conditions. The results from the temperature and humidity study revealed that the drug product is chemically and physically stable. Test results met the specifications under all tested conditions of temperature and humidity.

Physical Characteristics

The physical stability of the product was evaluated by assessing its appearance, water content and dissolution.

The specifications of the Appearance of the product was: white to pale yellow, translucent, rectangular film 20±2× 33±2 mm, and this specification was met throughout all timepoints of the stability study.

Water Content Results:

| Time point | 25° C./60% RH (as % w/w) Value 1; 2 | 30° C./65% RH (as % w/w) Value 1; 2 | 40° C./75% RH (as % w/w) Value 1; 2 |
| --- | --- | --- | --- |
| Initial | 3.48; 3.25 | (same as 25/60) | (same as 25/60) |
| 3 months | 2.72; 2.92 | NA | 2.68; 2.70 |
| 6 months | 3.26; 3.03 | NA | 2.98; 2.82 |
| 12 months | 3.30; 3.30 | 3.60; 3.60 | NA |

The dissolution of the film was evaluated at a single time point of 10 min. The results are shown in the table below.

Dissolution Test Results:

| Time point | 25° C./60% RH (% dissolved) Mean (N = 6); % RSD | 30° C./65% RH (% dissolved) Mean (N = 6); % RSD | 40° C./75% RH (% dissolved) Mean (N = 6); % RSD |
| --- | --- | --- | --- |
| Initial | 101; 3.4 | (same as 25/60) | (same as 25/60) |
| 3 months | 103; 3.0 | NA | NA |
| 6 months | 103; 2.6 | NA | NA |
| 12 months | 108; 1.8 | 106; 1.8 | NA |

Assay and Impurities

The content of dexamethasone and impurities were tested in triplicate and the average results are presented in the following tables. The specification of the product's assay was 7.2-8.8 mg (90.0-110.0% of LC), and this specification was met throughout all timepoints of the stability study.

Dexamethasone Assay Results:

| Time point | 25° C./60% RH Average % LC; % RSD; | 30° C./65% RH Average % LC; % RSD; | 40° C./75% RH Average % LC; % RSD; |
| --- | --- | --- | --- |
| Initial | 103.8; 4.1 | (same as 25/60) | (same as 25/60) |
| 3 months | 103.2; 1.8 | NA | 102.4; 2.9 |
| 6 months | 100.7; 2.5 | NA | 100.7; 1.5 |
| 12 months | 97.9 ; | 99.8 ; | NA |

Impurities Results:

| Time point | 25° C./60% RH Average Unknown; Average Total IMP | 30° C./65% RH Average Unknown; Average Total IMP | 40° C./75% RH Average Unknown; Average Total IMP |
| --- | --- | --- | --- |
| Initial | 0.15; 0.15 | (same as 25/60) | (same as 25/60) |
| 3 months | 0.15; 0.15 | NA | 0.15; 0.15 |
| 6 months | 0.15; 0.15 | NA | 0.15; 0.15 |
| 12 months | 0.12; 0.12 | 0.12; 0.12 | NA |

The results show that the product according to the invention is stable and no significant changes are observed in the assay. Moreover, no increase in degradation products is observed.

Example 4. Clinical Study of the Dexamethasone Oral Film According to the Invention In the following text, the dexamethasone film according to the invention is called the "Study Film", and the composition and preparation method were as described in Example 1.

A clinical study was made as a randomized, open label, two-period, two sequence, single dose, crossover study to evaluate the bioavailability, safety and tolerability following administration of Study Film 8 mg and Fortecortin 2×4 mg tablets to 30 healthy volunteers. The study consisted of a screening visit (visit 1), two consecutive residential treatment periods (visit 2 and 3) separated by a washout period and one end of study follow-up visit (visit 4). The primary objectives of this study were (i) To investigate single dose pharmacokinetics of dexamethasone in healthy volunteers after an oral administration of one Study Film strip, and (ii) To compare the single dose pharmacokinetics of Study Film with the single dose pharmacokinetics following oral administration of two Fortecortin tablets each of 4 mg. The secondary objective of this study was to investigate the short-term safety and tolerability of a single oral dose of Study Film.

The total duration for a subject was up to 31 days. A total of 30 healthy male adult subjects, between 19-37 years of age completed the study. Each subject received at one occasion a single oral dose of the test product Study Film (8 mg dexamethasone) and at another occasion the reference product Fortecortin tablets (2×4 mg dexamethasone). The visit schedule was:
   Screening visit (visit 1) 21 to 2 days prior to administration.
   Admission to clinical unit and Period 1 treatment (visit 2), day 1 to 3.
   Washout period 5 to 10 days after last pharmacokinetic (PK) sample (visit 2).
   Admission to clinical unit and Period 2 treatment (visit 3), day 1 to 3.
   Follow up visit (visit 4), 1 to 10 days after last PK sample (visit 3).

It should be mentioned that Fortecortin tablets were swallowed together with a glass of water (150 mL), whereas no water was given in case of the Study Film.

Pharmacokinetic Criteria for Evaluation were C(max), t(max), AUC(0-t) and AUC(0-∞) for dexamethasone in plasma. Safety Criteria for Evaluation were: Adverse events, concomitant medications, clinical chemistry, haematology, urinalysis, vital signs (blood pressure (BP), pulse rate and body temperature), electrocardiogram (ECG) and physical examination.

The descriptive statistical analysis for PK consisted of volunteer listings, graphs and summary statistics comprising geometric mean, coefficient of variation, arithmetic mean, standard deviation, median, minimum (min) and maximum (max) as appropriate. Tabulations and listings of data for vital signs, ECG, physical examinations, and clinical laboratory tests are presented. For clinical laboratory tests, listings of values for each volunteer are presented with abnormal or out-of-range values flagged. Bioequivalence between Study Film and Fortecortin was investigated using standard methods of calculations according to Bioequivalence guideline CPMP/EWP/QWP/1401/98. Differences in bioavailability (AUC), C(max) and t(max) were tested using ANOVA and a nonparametric test as appropriate. Data from all the assayed subject samples that completed the study was included in the statistical analysis. All randomised subjects who received doses of the both investigational products were included in the statistical evaluation.

Figure 1A:
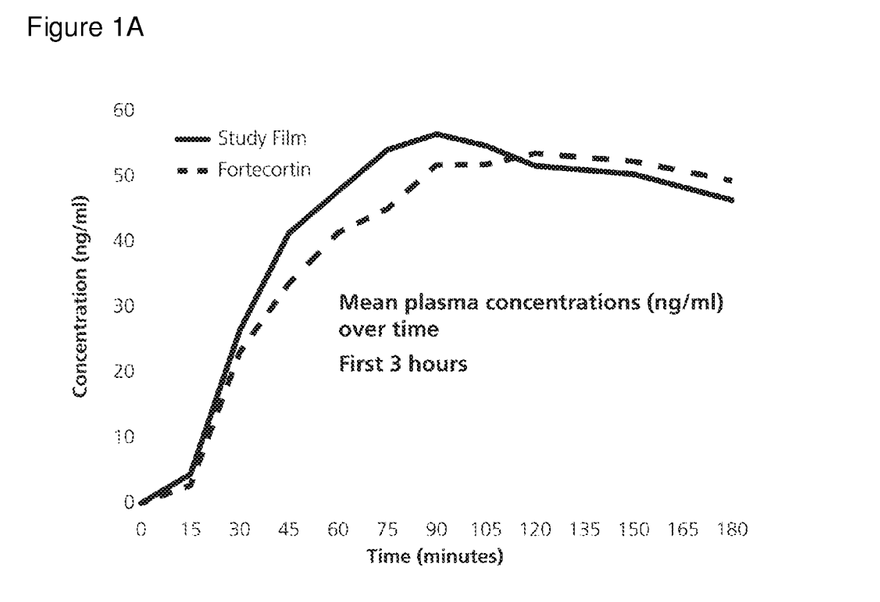
Figure 1B:
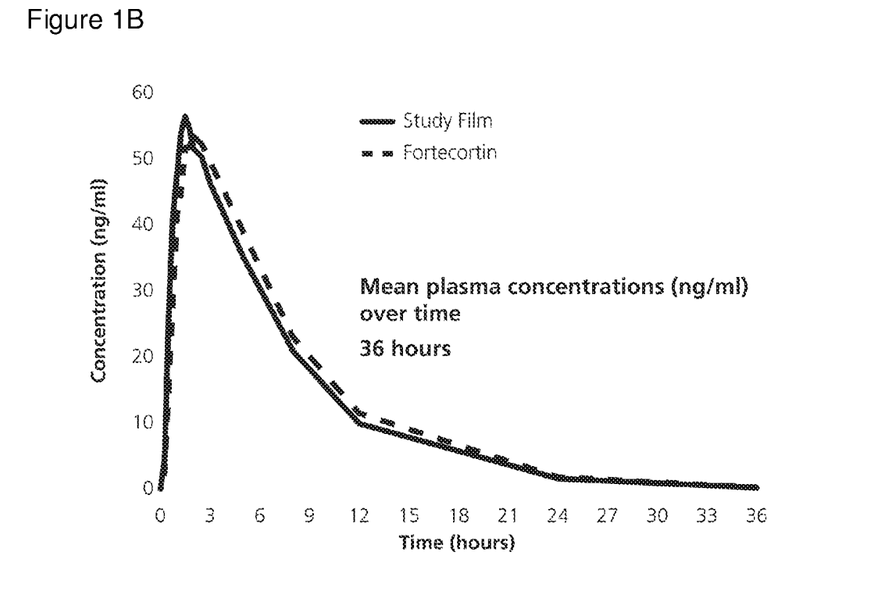

Thirty-five healthy volunteers were screened of which 30 were enrolled and randomised. The first healthy volunteer entered the study on 10 Jun. 2013 and the last healthy volunteer finished the study on 4 Sep. 2013. In total, 30 healthy volunteers were administered test product and reference product. All randomized healthy volunteers completed the study. There were no protocol deviations that led to the exclusion of data from the PK or safety analyses. The safety and PK analysis sets included all randomized healthy volunteers. The results are shown in FIGS. 1A and 1B.

Based on the data and results from this study, the study conclusions became:
   Study Film was bioequivalent to Fortecortin as the 90% confidence intervals were within the acceptance limits (0.8, 1.20) for the parameters tested ($AUC_{0-t}$, $AUC_{0-\infty}$ and C(max))
   The C(max) of dexamethasone in Study Film was reached after 1.3 h
   The median t(max) for Study Film was found to be 23 minutes shorter than t(max) for Fortecortin
   The terminal half-life ($t_{1/2}$) of dexamethasone was approximately 4 h
   The single dose Study Film was considered to be safe and tolerable within the conditions used in this study. No serious adverse events and only mild and moderate (one) adverse events were reported. Laboratory variables showed no clinically relevant or treatment related abnormalities.

Comparative Example 1

To investigate the systemic absorption from dexamethasone films with other compositions than those in the current invention, and in which the dexamethasone was dissolved rather than dispersed as particles as in the present invention, and in which only a lower drug load could be achieved (only about 10% instead of for example 40% as in the present invention), a pharmacokinetic study in Syrian hamster was made.

Three different dexamethasone film compositions (A, B and C, see below) were included in the study. The three compositions had been chosen based on an assumption that bioadhesivity to the oral mucosa would be an advantage for fast systemic absorption. A control formulation was not used in the pharmacokinetic study.

| Ingredient | A | B | C |
| --- | --- | --- | --- |
| Dexamethasone | 10% | 10% | 10% |
| Polysorbate 80 | 1% | 1% | 1% |
| Metolose 60SH-50 | 44.5% | 40.9% | 33.7% |
| Pharmacoat 603 | 44.5% | 40.9% | 33.7% |
| Eucalyptol | 0 | 3.9% | 11.6% |
| L-menthol | 0 | 2.7% | 8.2% |
| Racemic (DL) menthol | 0 | 0.6% | 1.8% |

All percentages are % w/w based on dry weight

The film compositions were prepared essentially as described in Example 1. However, dexamethasone was dissolved in a 2:1 mixture of ethanol and water before addition of the other ingredients, and dexamethasone remained dissolved in the films. The ethanol-water mixture thus had the same role as process solvent as has water in the present invention. Compared with the film composition described in Example 1, dexamethasone was thus dissolved in the film, and present in a much lower concentration than in Example 1 (10% w/w vs 40% w/w). Given that a small animal model was used, the compositions A-C used contained 1.1 mg of dexamethasone and the size of the film units employed were 1.0 cm$^2$. However, the area concentration of dexamethasone was about the same as the current invention i.e. about 1.2 mg per cm$^2$.

The study was performed in 58 Syrian Hamsters (LAK: LVG (SYR) BR from Charles River Deutschland GmbH, Sulzfeld, Germany. Eight extra animals were available for replacement purposes.

Before treatment the cheek pouches were rinsed, using a physiological saline solution and examined for abnormalities using an otoscope. The test formulation was placed in the most distal end of the left cheek pouch, using an otoscope and a fixing device. A collar was placed around the neck of the animal (to avoid the animal from storing the food in the pouches which could damage the cheek pouch mucosa) and the animal was returned to its cage. The test formulation was left in the cheek pouch for dissolving. On day 1, blood samples were taken from all animals in Group 5. Blood sampling was performed at the following time points: 30 min, 1, 2, 4, 5 and 8 hours post-treatment. Blood samples of approximately 0.5 ml were drawn from the orbital venous plexus during $CO_2/O_2$ anaesthesia. The blood was sampled into a collecting tube containing EDTA, K3 as anticoagulant. The collecting tube was placed in ice water until centrifugation (10 min, 1270 G, +4° C.). The plasma was transferred to cryotubes (Ninc, Denmark) and frozen at −18° C. or below until analysis. The plasma samples were analysed using a quantitative method for the determination of dexamethasone in hamster plasma by liquid chromatography coupled to tandem mass spectrometry (UPLC-MS/MS). The calibration curve was in the range of 20-11000 ng/ml with a lower limit of quantification of 20 ng/ml.

The result from the study showed that no reliable values of plasma dexamethasone were obtained as they were all below the lower limit of quantification. Thus, in conclusion no or only very small and undetectable amounts of dexamethasone was absorbed into the systemic circulation from the film compositions tested. It was concluded that the tested compositions were not feasible for their purpose which was to achieve as high, reliable and fast systemic absorption of dexamethasone.

Comparative Example 2

To investigate the optimal composition of the oral film with regard to (i) handling and mechanical properties, (ii) in vivo disintegration rate, and (iii) in vivo bioadhesion, a series of tests were performed with differently composed films.

With "handling and mechanical properties" is meant the performance of the film from the user's perspective when the film is taken out of the package and being administered to the oral cavity. With "in vivo disintegration rate" is meant the rate at which the film disintegrates and disappears as experienced by a test person, i.e. a subjective sensory based measure which is expressed in seconds. With "in vivo bioadhesion" is meant the tendency of the test product to adhere to the gum to teeth or to other parts of the oral cavity, said adherence competing with the desired fast disintegration, or being perceived by the test person to do so or otherwise being a negative phenomenon.

These characteristics were investigated by a sequential test procedure that involved: (1) the test person opening the sealed pouch with a scissor and taking out the film sample, (2) then holding the film sample between thumb and index finger in left hand for about 30 seconds, (3) then moving it to the right hand between thumb and index finger, (4) then placing the film sample onto the tongue, (5) then closing the mouth and keeping it closed for about 5 seconds, and (6) finally slowly opening mouth again and from that timepoint trying not to swallow and trying to do neither more nor less movements in the oral cavity than usual.

The readouts and observations made were: (a) did the film piece stick to the fingers?, (b) was it brittle?, (c) was it too flexible and/or bending too easily?, (d) how fast did it apparently disintegrate after closing the mouth?, and (e) how did it appear in the mouth if not disintegrating (e.g. did it adhere to the mucosa or form lumps etc.)?. The test was designed as crossover, i.e. one and the same test person tested all products. Written notes were taken.

The tables below describe compositions subjected to the above test procedure. The film compositions had been prepared essentially as described in Example 1. The alginate used was Protanal LFR 5/60. Pullulan is a polysaccharide polymer consisting of maltotriose units, produced from starch by the fungus *A. pullulans* and is an edible, tasteless polymer which chief commercial use is in the manufacture of edible films that are used as breath freshener or oral hygiene products. As a food additive, it is also known as E1204. The ethyl cellulose was in microcrystalline form and had been included as a substitute for the active ingredient dexamethasone, to avoid that the test persons had to ingest dexamethasone during test procedure steps (4) to (6). The thickness was calculated from area weight with the assumption that density was 1.2 g/cm3

To validate the use of ethyl cellulose as a proxy for dexamethasone (for the purpose of these tests), an abbreviated test procedure was initially used that included only steps (1) to start of (5) but then interrupting and making an thorough oral wash. Samples tested were D12:102 and D12:104 (both containing dexamethasone) versus D12:98b and D12:100, respectively, (both containing ethyl cellulose). That initial testing confirmed that ethyl cellulose was an appropriate proxy for dexamethasone. It also confirmed that the abbreviated test procedure was an acceptable substitute for the full procedure, and hence it was used also for other dexamethasone containing sample to spare test persons from unnecessary dexamethasone exposure.

| Ingredient | Composition (% w/w of dry weight) | | | | | |
| --- | --- | --- | --- | --- | --- | --- |
| | O12:1 | O12:2 | D12:98a | D12:98b | D12:99a | D12:99b |
| Dexamethasone | 30.0 | 30.0* | | | | |
| Ethyl cellulose | | | 37.5 | 37.5 | 50.0 | 50.0 |
| Metolose 60SH-50 | | | 62.5 | 62.5 | 50.0 | 50.0 |
| Pharmacoat 603 | | | | | | |
| Pullulan | 70.0 | 70.0 | | | | |
| Alginate | | | | | | |

| | Composition (% w/w of dry weight) | | | | | |
|---|---|---|---|---|---|---|
| Ingredient | O12:1 | O12:2 | D12:98a | D12:98b | D12:99a | D12:99b |
| PEG 3350 | | | | | | |
| Area (cm2) | 8 | 8 | 8 | 6 | 8 | 6 |
| Area weight (g/m2) | 33 | 33 | 27 | 36 | 20 | 27 |
| Thickness (μm) | 28 | 28 | 22 | 30 | 17 | 22 |

*dexamethasone sodium phosphate

| | Composition (% w/w of dry weight) | | | | | |
|---|---|---|---|---|---|---|
| Ingredient | D12:100 | D12:101 | D12:102 | D12:103 | D12:104 | D12:105 |
| Dexamethasone | | | 37.5 | 50.0 | 37.5 | 50.0 |
| Ethyl cellulose | 37.5 | 50.0 | | | | |
| Metolose 60SH-50 | 31.2 | 25.0 | 62.5 | 50.0 | 31.2 | 25.0 |
| Pharmacoat 603 | 31.2 | 25.0 | | | 31.2 | 25.0 |
| Pullulan | | | | | | |
| Alginate | | | | | | |
| PEG 3350 | | | | | | |
| Area (cm2) | 6 | 6 | 6 | 6 | 6 | 6 |
| Area weight (g/m2) | 36 | 27 | 36 | 27 | 36 | 27 |
| Thickness (μm) | 30 | 22 | 30 | 22 | 30 | 22 |

O12:1 and O12:2 were tested with regard to in vivo disintegration which was fast. However, certain samples were accidentally left at ambient air humidity conditions without container, which apparently caused humidity to be absorbed into the samples which then became somewhat sticky and also raised concerns about chemical stability of the drug substance. When dried again in an oven at about 45-60° C. for about 30 minutes and cooled again in controlled humidity the samples had become brittle. It was concluded that O12:1 or O12:2 did not represent ideal compositions.

D12:98a, D12:98b, D12:99a, D12:99b, D12:100 and D12:101 were subjected to the above test procedure. It had been hypothesized that fine tuned addition of Pharmacoat, which has lower viscosity than Metolose, could render the ideal character. The mechanical properties appeared good for all six except for D12:99a, D12:99b and D12:101 which were somewhat too flimsy for handling. For D12:98a, D12:98b, and D12:99b the vivo disintegration rate was acceptable, but slower than desired and was estimated to 2-3 minutes or more. It was also noted for these samples that lumps of undissolved film or unintentionally folded film were formed. To some but less extent also D12:100 suffered from this lump formation and bioadhesion. Samples D12:100 and D12:101 were judged as best in this group of six, but all were acceptable.

D12:102, D12:103, D12:104 and D12:105 were subjected to testing of mechanical properties and in vivo disintegration rate. The mechanical properties appeared acceptable for all samples, but best for D12:102 and D12:104. For D12:102 and D12:103 the vivo disintegration rate was acceptable, but slower than desired, around at least 2-3 minutes and lumps of undissolved or folded film o were formed just as described above for D12:98a and others. Sample D12:105 was judged as being second best, but the clearly best in this series was D12:104.

| | Composition (% w/w of dry weight) | | | | | | | |
|---|---|---|---|---|---|---|---|---|
| Ingredient | J13:106a | J13:106b | J13:108a | J13:108b | J13:109a | J13:109b | F13:1 | F13:2 |
| Dexamethasone | | | | | | | | 40.0 |
| Ethyl cellulose | 37.5 | 37.5 | 37.5 | 37.5 | 37.5 | 37.5 | 40.0 | |
| Metolose 60SH-50 | 12.5 | 12.5 | 12.5 | 12.5 | 20.0 | 20.0 | 30.0 | 30.0 |
| Pharmacoat 603 | 50.0 | 50.0 | 37.5 | 37.5 | 30.0 | 30.0 | 30.0 | 30.0 |
| Pullulan | | | | | | | | |
| Alginate | | | 12.5 | 12.5 | | | | |
| PEG 3350 | | | | | 12.5 | 12.5 | | |
| Area (cm2) | 8 | 5 | 8 | 5 | 8 | 5 | 6.6 | 6.6 |
| Area weight (g/m2) | 27 | 43 | 27 | 43 | 27 | 43 | 30 | 30 |
| Thickness (μm) | 22 | 36 | 22 | 36 | 22 | 36 | 25 | 25 |

J13:106a, J13:106b, J13:108a, J13:108b, J13:109a, J13:109b, F13:1 and F13:2 were subjected to testing of mechanical properties and in vivo disintegration rate. It was hypothesized that alginate and PEG3350 would work as disintegrating agents in J13:108a&b and J13:109a&b, respectively. The mechanical properties appeared good except that J13:108a and J13:108b felt slightly sticky when handled, presumably due to the alginate. All the three 8 cm2 samples felt considerably thinner and flimsier but not so much that they were ruled out. The vivo disintegration rate for J13:109a and J13:109b was, surprisingly, slower than for the others, despite the PEG content. Moreover, both J13:109a and J13:109b, and in particular the latter, had the same problems with lumps and undesired bioadhesivity as reported for other samples above. It was concluded that J13:108a, J13:108b, J13:109a or J13:109b did not represent ideal compositions. Surprisingly, J13:108a and J13:108b also showed a rather strong bioadhesivity and tended to stick to the upper palate during step 6 in the test protocol described above, to an extent that made them less feasible because that phenomenon slowed down the dissolution and could make the patient feel uncomfortable. Samples J13:106a and J13:106b were easy to handle, e.g. appeared non-hygroscopic and non-sticking, showed fast dissolution in vivo (<20 seconds) and exhibit only minor problems with lump formations or unwanted bioadhesivity. The clearly superior samples were however F13:1 and F13:2, which were easy to handle, e.g. appeared non-hygroscopic and non-sticking, showed fast dissolution in vivo (<10 seconds) and did not exhibit any problems with lump formations or bioadhesivity.

Accordingly, this long test series led to a feasible formulation according to the present invention such as represented by F13:2.

Comparative Example 3

A set of studies is made on human healthy volunteers, under medical supervision at a hospital.

In a first set of studies, each of composition A, B and C, as described in Comparative example 1 above, is tested on N=3 subjects. Test pieces of 2 cm$^2$ are cut out representing a dose of 2 mg. The test pieces are placed in a buccal position, at the inside of the lower lip and in close contact with the buccal mucosa at both sides. Plasma samples are withdrawn at 0, 15, 30, 45, 60, 90 and 120 minutes and are analysed with a method described in Materials and Methods above. A total of nine plasma curves are thus generated. It is hypothesized, based on literature values, that the C(max) will be in the order of 46 nmol/L, and that t(max) will be well below 90 minutes for one or more of these compositions. Surprisingly, it is found that only one out of a total 9 plasma curves exhibit a C(max) above 30 nmol/L, and that only one of the nine C(max) is below 90 minutes. Most curves present such slow absorption rate that C(max) is not even reached within the 120 minutes that the sampling lasted. Furthermore, there is high inter- and intrasubject variability, and there is no consistent pattern as how t(max) ranks between A, B and C. It is concluded that the compositions A, B and C are not feasible for their purpose.

In a second set of studies, 2 cm2 test pieces of said composition A are tested on N=2 subjects and at three different administration sites: (a) in a sublingual position, (b) in a buccal position such as described in the previous set of experiments, and (c) in buccal but very distant pocket-like position inside the upper lip from which the leakage of saliva into other parts of the oral cavity. Plasma samples are withdrawn at 0, 15, 30, 45, 60, 90, 120, 150 and 180 minutes and are analysed with a method described in Materials and Methods above. A total of six plasma curves are thus generated. It is hypothesized that one or more of these plasma curves will show beneficial results such as C(max) in the order of 46 nmol/L or t(max) below 90 minutes. The results show that (a) exhibits a somewhat higher and faster systemic absorption than (b) but both are rather similar to that of the first set of studies, i.e. the anticipated C(max) and t(max) values re not achieved. It is further found that (c) does not exhibit any measurable plasma levels whatsoever, i.e. similar to the findings in Comparative example 1. Despite testing different administration positions, the plasma curves are thus not satisfactory. It is now concluded that compositions A, B and C are unfeasible.

Comparative Example 4. Exploratory Stability Study of Films Containing Dissolved Dexamethasone Samples of compositions A, B and C prepared essentially as described in Comparative example 1, were subject to characterization and exploratory stability testing with a special focus on assay (dexamethasone content) and degradation products and impurities ("related substances"). The method used was essentially that described in Methods and Materials except for certain modifications related to the different compositions and excipients.

Dexamethasone content was 8.2, 8.3 and 8.6 mg per unit, respectively, after manufacturing, but had decreased to 7.4, 7.8 and 8.4 mg per unit, respectively, after just 7 weeks storage at 40 C.

Within less than 7 weeks after manufacturing the sum of the three largest peaks of related substances were 0.98, 0.94 and 0.93 (as % peak area) for A, B and C, respectively, and this was considered high and not feasible.

The invention claimed is:

1. A unit dose disintegrating oral film for delivering dexamethasone into the gastrointestinal tract, comprising dexamethasone in micronized form dispersed in a hydroxypropyl methylcellulose matrix, wherein the concentration of dexamethasone in the film is 30% w/w or more and the concentration of hydroxypropyl methylcellulose in the film is between 35 and 70% w/w, all based on total dry matter, wherein the hydroxypropyl methylcellulose is a mixture of two or more hydroxypropyl methylcelluloses of differing viscosity, and wherein, when subject to dissolution testing prior to storage in accordance with USP <711> Dissolution, Apparatus 2 using the alternative sinkers and a dissolution medium of 0.2% aqueous sodium lauryl sulphate, 100% w/w of the dexamethasone is released from the film when measured at 10 minutes.

2. An oral film according to claim 1, wherein the sum of the concentrations of dexamethasone and hydroxypropyl methylcellulose is from 95% to 100% w/w.

3. An oral film according to claim 1, wherein the hydroxypropyl methylcelluloses are of a pharmaceutical grade hydroxypropyl methylcellulose.

4. An oral film according to claim 1, wherein the hydroxypropyl methylcelluloses comprise hydroxypropyl methylcellulose type 2910.

5. An oral film according to claim 1, wherein the hydroxypropyl methylcellulose is a mixture of two hydroxypropyl methylcelluloses having different viscosity, wherein the concentrations of the two hydroxypropyl methylcelluloses in the film are the same.

6. An oral film according to claim 1, wherein the hydroxypropyl methylcellulose is a mixture of hydroxypropyl methylcelluloses having a viscosity of 3 mPa·s and 50 mPa·s, respectively.

7. An oral film according to claim 1, wherein the concentration of dexamethasone is from 35 to 45% w/w.

8. An oral film according to claim 7, wherein the concentration of dexamethasone is 40% w/w.

9. An oral film according to claim 1, wherein the total concentration of hydroxypropyl methylcellulose is from 55 to 65% w/w.

10. An oral film according to claim 1, wherein the hydroxypropyl methylcellulose is a mixture of two hydroxypropyl methylcelluloses having a viscosity of 3 mPa·s and 50 mPa·s, respectively, wherein the total concentration of the mixture is 60% w/w.

11. An oral film according to claim 1, wherein the dexamethasone in micronized form has a particle size distribution by volume such that:
≥80% of the particles have a size of ≤5 μm,
≥99% of the particles have a size of ≤15 μm, and
100% of the particles have a size of ≤30 μm.

12. An oral film according claim 1, wherein the film has a thickness of from 15 to 50 μm.

13. An oral film according to claim 1, wherein the unit dosage form contains from 4 to 10 mg of dexamethasone.

14. An oral film according to claim 1, wherein the dexamethasone in micronized form has a particle size distribution by number such that:
≥90% of the particles have a size of ≤5 μm, and
100% of the particles have a size of ≤15 μm.

15. A method of treating a condition selected from chemotherapy induced nausea, chemotherapy induced vomiting, croup, acute allergic conditions, anaphylactic conditions, brain oedema, and high-altitude disease, comprising orally administering an oral film according to claim 1 to a subject in need thereof.

16. A method for preparing an oral film according to claim 1, comprising:
(i) dispersing dexamethasone in water to obtain a dispersion,
(ii) dissolving hydroxypropyl methylcellulose in the dispersion,
(iii) coating the dispersion resulting from step (ii) on an intermediate layer to obtain a wet film,
(iv) drying the wet film, and
(v) removing the intermediate layer.

17. A method for preparing an oral film according to claim 1, comprising:
(i) dissolving hydroxypropyl methylcellulose in water to obtain a homogeneous viscous solution,
(ii) dispersing dexamethasone in the solution to obtain a homogeneous viscous dispersion,
(iii) coating the dispersion resulting from step (ii) on an intermediate layer to obtain a wet film,
(iv) drying the wet film, and
(v) removing the intermediate layer.

* * * * *